(12) United States Patent
Gisep et al.

(10) Patent No.: US 8,475,464 B2
(45) Date of Patent: Jul. 2, 2013

(54) CANNULA

(75) Inventors: Armando Gisep, Davos Dorf (CH); Vanessa Boner, Klosters (CH); Norbert Suhm, Davos Wolfgang (CH)

(73) Assignee: AO Technology AG, Chur (CH)

( * ) Notice: Subject to any disclaimer, the term of this patent is extended or adjusted under 35 U.S.C. 154(b) by 262 days.

(21) Appl. No.: 12/663,031

(22) PCT Filed: May 27, 2008

(86) PCT No.: PCT/CH2008/000238
§ 371 (c)(1),
(2), (4) Date: Jan. 8, 2010

(87) PCT Pub. No.: WO2008/148232
PCT Pub. Date: Dec. 11, 2008

(65) Prior Publication Data
US 2010/0145277 A1  Jun. 10, 2010

(51) Int. Cl.
*A61B 17/58* (2006.01)
(52) U.S. Cl.
USPC ............................................................ 606/92
(58) Field of Classification Search
USPC ..................... 606/92–95; 604/35, 43, 164.11, 604/912
See application file for complete search history.

(56) References Cited

U.S. PATENT DOCUMENTS

| | | | |
|---|---|---|---|
| 2,833,280 A * | 5/1958 | Hein, Jr. ........................ | 604/89 |
| 5,037,423 A | 8/1991 | Kenna | |
| 5,133,771 A * | 7/1992 | Duncan et al. ............... | 623/23.2 |
| 5,976,104 A | 11/1999 | Wolfinbarger, Jr. | |
| 6,730,095 B2 | 5/2004 | Olson, Jr. et al. | |

(Continued)

FOREIGN PATENT DOCUMENTS

| | | |
|---|---|---|
| JP | 10-505253 A | 5/1998 |
| JP | 2004-501716 A | 1/2004 |

(Continued)

OTHER PUBLICATIONS

Majkowski, R.S. et al.; "Bone Surface Preparation in Cemented Joint Replacement"; The Journal of Bone and Joint Surgery; May 1993; pp. 459-463; vol. 75-B, No. 3; British Editorial Society of Bone and Joint Surgery.

*Primary Examiner* — Kevin T Truong
*Assistant Examiner* — Diana S Jones
(74) *Attorney, Agent, or Firm* — Rankin, Hill & Clark LLP

(57) ABSTRACT

A cannula (1) comprising A) a central axis (2), a front end (3), a rear end (4) and a channel (5) coaxial or parallel to said central axis (2) and defining a peripheral wall (12) of said cannula (1); B) referencing means (15) at said rear end (4), so that said cannula (1) can be brought in a desired position relative to a cavity (120) in a bone; wherein C) said cannula (1) further comprises at least two perforations (8) penetrating said peripheral wall (12) transversely to said central axis (2); and D) said at least two perforations (8) are arranged in a portion (16) of said peripheral wall (12) which extends over an arc (18) orthogonal to said central axis (2) with a central angle $\alpha < 270°$. A method for applying bone cement into a bone structure comprising the steps of: A) selecting at least one region in a bone where the trabecular bone structure is to be augmented; B) producing at least one cavity (120) communicating with said at least one bone region; C) applying a fluid jet lavage towards said at least one bone region, and D) providing bone cement to said at least one bone region.

21 Claims, 5 Drawing Sheets

| U.S. PATENT DOCUMENTS | | | |
|---|---|---|---|
| 6,960,215 B2 | 11/2005 | Olson, Jr. et al. | |
| 7,488,320 B2 | 2/2009 | Middleton | |
| 2002/0156420 A1 | 10/2002 | Anderson et al. | |
| 2003/0083662 A1 | 5/2003 | Middleton | |
| 2004/0002713 A1 | 1/2004 | Olson, Jr. et al. | |
| 2006/0079905 A1 | 4/2006 | Beyar et al. | |
| 2007/0055282 A1* | 3/2007 | Muschler | 606/92 |

| FOREIGN PATENT DOCUMENTS | | |
|---|---|---|
| JP | 2005-501649 A | 1/2005 |
| WO | 96/00524 A1 | 1/1996 |
| WO | 02/02033 A1 | 1/2002 |
| WO | 03/022165 A1 | 3/2003 |
| WO | 2006/011152 A2 | 2/2006 |
| WO | 2007/028120 A2 | 3/2007 |

* cited by examiner

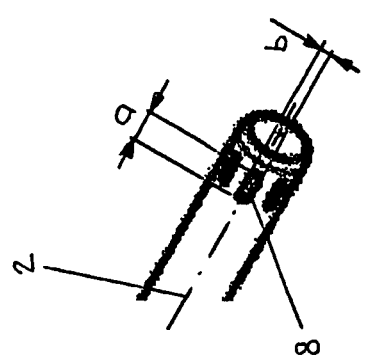
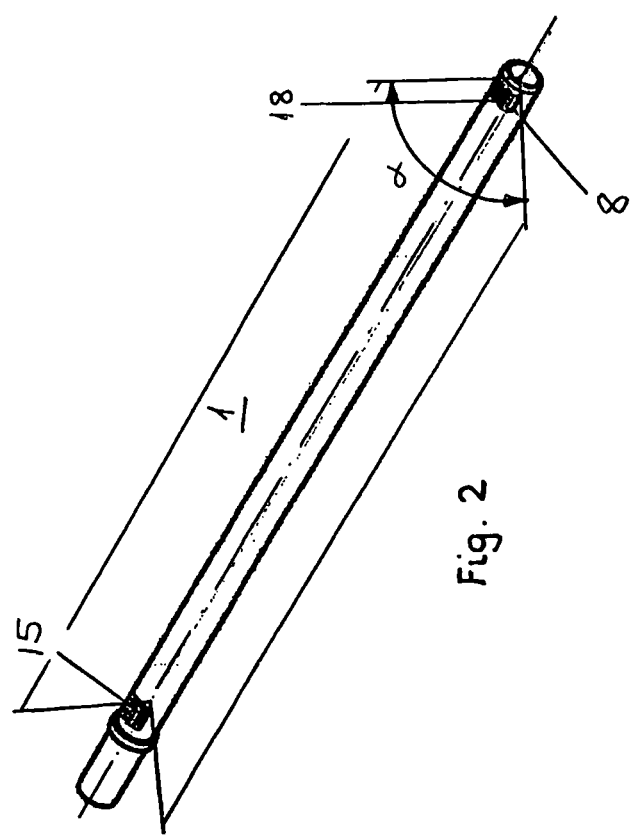

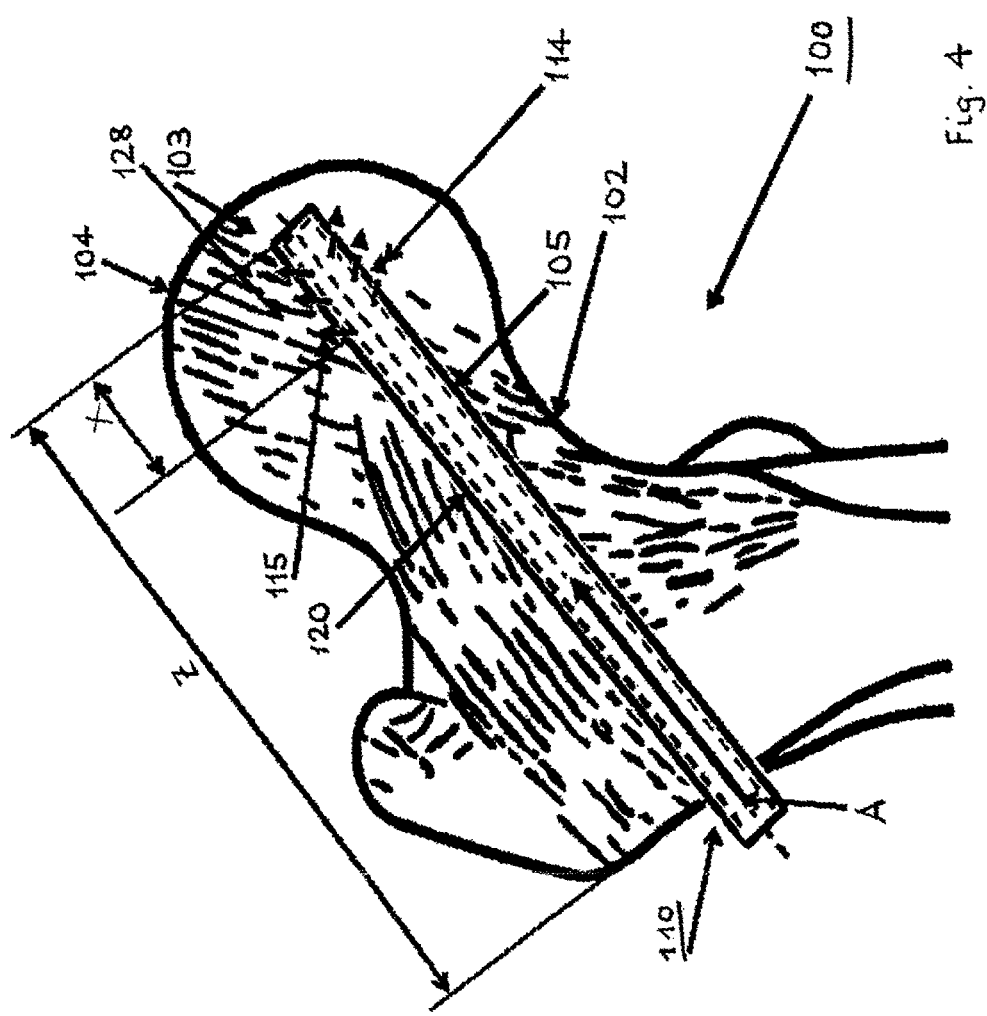

CANNULA

CROSS REFERENCE TO RELATED APPLICATIONS

This application is a U.S. national stage of international application PCT/CH2008/000238, filed May 27, 2008, which claimed priority to U.S. application Ser. No. 11/757,781, filed Jun. 4, 2007, now abandoned.

1. Field of the Invention

The invention relates to a cannula and to a method for applying bone cement into a bone structure.

In orthopedic surgery implant cut-out after osteosynthesis, e.g. treatment of proximal femur fractures or femoral neck fractures is a major complication often leading to severe and sometimes lethal complications. The rate of implant cut-out was significantly reduced in the past by changing from mostly rigid fixation principles to dynamically active devices such as e.g. the dynamic hip screw. However, the number of failed fixations remains high for comminuted fractures in osteoporotic proximal femurs. Therefore, an urgent need for improvement of implant fixation remains.

Augmentation of the cancellous bone structure with bone cements has proven to enhance the performance of a fixation. Further, in arthroplasty surgeries e.g. hip joint replacement surgery it is known that irrigation of bone has been investigated and carried out for better interdigitation of bone cements with cortical or cancellous bone leading to a significantly better cement penetration in in-vitro and in-vivo.

2. Description of the Prior Art

A study concerning the effects of bone surface preparation on bone cement penetration has been published by: R. S. MAJKOWSKI et al. "Bone surface preparation in cemented joint replacement", The Journal of Bone and Joint Surgery, Vol. 75-B, No. 3, May 1993. This document is related to bone surface preparation in cemented joint replacement. The disclosure particularly concerns the penetration depth of bone cement into the trabecular structure of a bone. The penetration of the applied bone cement into the trabecular structure depends on the extent of marrow removal from the bone interstices. It has been found that compared to unprepared bone with a mean penetration depth of 0.2 mm a mean penetration depth of between 4.8 to 7.9 mm can be achieved by use of pressurized fluid jet lavage for a bone surface preparation. A pressurized fluid jet lavage uniformly applied to the bone structure to be prepared results in an equal irrigation of areas with a sparse distribution of trabeculae and areas with a dense distribution of trabeculae such that a bone cement subsequently injected would preferably penetrate in that portion with the sparse distribution of trabeculae, i.e. it would follow the path of least resistance into the region with larger bone interstices.

Furthermore, there are many approaches as to load biodegradable bone cements with different kinds of bioactive substances and/or pharmaceuticals. Mostly, bone cements have to be loaded with excessive amounts of therapeutic agents due to inaccurate placement and distribution in the bone structure of the bone cement. This leads to undesired local and systemic reactions to the drug. Further, inaccurate cement placement leads to more material being used, a fact that is not tolerable with this sort of expensive bioactive material.

SUMMARY OF THE INVENTION

It is an object of the invention to provide a device and a method for introducing freshly mixed bone cement into a cavity such that the bone cement penetrates differentially into the surrounding bone structure.

The invention solves the posed problem with a cannula and with a method for applying bone cement into a bone structure.

The cannula according to the invention essentially has the advantages of:

due to more than one perforation a sufficient rigidity of the peripheral wall is ensured over the whole length of the cannula; and due to the asymmetrical arrangement of the perforations the cannula can be used for a fluid jet lavage at selected regions only of the bone structure surrounding a cavity previously produced in the bone.

In one embodiment of the cannula the sum of cross sectional areas of the entirety of said perforations is smaller than or equal to the cross sectional area of said channel.

In a further embodiment said perforations are arranged in at least two sections which are axially distanced from each other.

In another embodiment said perforations are staggeredly arranged with respect to said central axis.

In yet a further embodiment said cannula comprises between two and ten perforations arranged in said portion of said peripheral wall.

In still another embodiment said cannula has no handle.

In a further embodiment said referencing means comprises a marking on the peripheral surface of said cannula and arranged at said rear end of said cannula indicating the angular position of said arc of said peripheral wall viewed in a cross-section of said cannula orthogonal to said central axis.

In another embodiment said referencing means is located in such manner that it indicates the point of symmetry of said arc of said peripheral wall.

In still another embodiment said referencing means is located and configured in such manner that it completely extends between the lateral limitations of said arc of said peripheral wall.

In yet a further embodiment each of said perforations has a cross sectional area of minimum 0.1 mm$^2$, preferably of minimum 0.2 mm$^2$.

In another embodiment each of said perforations has a cross sectional area of maximum 80 mm$^2$, preferably of maximum 40 mm$^2$.

In still a further embodiment the sum of all cross sectional areas of said perforations is minimum 0.2 mm$^2$, preferably minimum 0.4 mm$^2$.

In another embodiment the sum of all cross sectional areas of said perforations is maximum 800 mm$^2$, preferably maximum 400 mm$^2$.

In still another embodiment no perforations penetrate said peripheral wall of said cannula in the remaining part outside said portion of said peripheral wall.

In a further embodiment said at least two perforations are arranged in a front part of said cannula.

In a further embodiment said cannula has a length L measured parallel to said central axis and said portion of said peripheral wall extends over a length I in a range between 5% and 30% of said length L measured from said front end of said cannula.

In yet a further embodiment said central angle α of said portion of said peripheral wall is greater than 30°, preferably greater than 60°. In case of a small central angle said perforations can be staggeredly arranged.

In another embodiment said perforations are elongated holes with their long axes in the direction of said central axis.

In still another embodiment said elongated holes have a length a measured parallel to said central axis and a width b measured orthogonal to said central axis and wherein the ration b:a of said width b to said length a is in a range between 0.1 and 0.5.

In another embodiment said perforations are all located at the same distance A from said front end of said cannula.

In a further embodiment said cannula is axially closed at said front end.

In a further embodiment said cannula additionally comprises a wire, wherein
a) said channel is axially open at said front end; and
b) the cross section of said channel has a contraction with a diameter $d_r$ located between the front most of said at least two perforations and said front end which is formed as a sealing between said wire and said channel.

The kit for liquid jet irrigation of bone comprises one of the above embodiments of said cannula and a liquid jet washing apparatus including at least a pump and a control means.

In another embodiment said liquid jet is generated in a pulsed manner.

In a further embodiment said liquid jet is generated with a minimum frequency of 1300 pulses/min., preferably of 1400 pulses/min.

In a further embodiment said liquid jet is generated with a maximum frequency of 1700 pulses/min., preferably of 1600 pulses/min.

In yet a further embodiment the maximum duration of one jet lavage pulse is 0.015 s, preferably 0.011 s.

In another embodiment the minimum duration of one jet lavage pulse is 0.005 s, preferably 0.009 s.

In another embodiment the interval between two jet lavage pulses is at least 0.02 s, preferably at least 0.025 s.

In another embodiment the interval between two jet lavage pulses is at most 0.04 s, preferably at most 0.035 s.

In still another embodiment the jet lavage is performed with a maximum speed of the lavage liquid of 55 m/s, preferably of 51 m/s.

In a further embodiment the jet lavage is performed with a minimum speed of the lavage liquid of 45 m/s, preferably of 49 m/s.

In a further embodiment the maximum penetration depth of the jet lavage liquid is 16 mm, preferably 14 mm.

In a further embodiment the kit additionally comprises at least one bone fixation implant.

In a further embodiment the kit additionally comprises at least one package of unmixed bone cement.

In yet a further embodiment the kit additionally comprises at least one container with washing solution, preferably a Ringer solution.

One of the advantages of the method according to the invention is that the fluid jet lavage at selected regions only of the bone structure surrounding a previously produced cavity in the bone allows a controlled penetration and distribution of the bone cement in regions of the bone structure where a reinforcement of the trabecular structure is desired. For example, this allows to augment the bone structure at desired regions in order to enhance purchase to an implant (prophylactic and/or traumatic).

Other indications of the method according to the invention could be metaphyseal parts of long bones as well as vertebral bodies of the spine.

The entire method allows for minimally invasive interventions for least iatrogenic trauma, which is considered to be key for a prophylactic treatment.

In one preferred embodiment said fluid jet lavage is applied selectively to said at least one bone region.

In another embodiment said fluid jet lavage is applied in such a manner that it produces a desired differential lavage of said bone structure such that said bone cement penetrates differentially and intensified at said at least one bone region into said bone structure.

In a further embodiment said fluid jet lavage is applied with a variable intensity to the entirety of said bone structure and preferably with a higher intensity towards said at least one bone region.

In yet another embodiment said fluid jet lavage is applied with a constant intensity at said at least one bone region only.

In a further embodiment the bone cement is provided to said at least one bone region by introducing a freshly mixed bone cement into said cavity by means of a radially perforated cannula. The advantage of this embodiment is that a cannula sealed against the bone apart from the radial perforations allows for the application of the bone cement and to apply some pressure to the cement in order to achieve an infiltration of the cleaned-out trabecular network and achieve the asymmetrical cement distribution. The cannula can be placed at the entry of the created cavity to inject the bone cement or can be advanced all the way to the bottom of the created cavity, injecting the cement in a retrograde manner.

In yet another embodiment the bone cement is provided to said at least one bone region by introducing a freshly mixed bone cement into said cavity by means of a cannulated and radially perforated implant.

In still a further embodiment the bone cement is provided to said at least one bone region by filling said cavity with a bone cement and displacing the cement by inserting an implant into said cavity.

In a further embodiment said pre-selected at least one bone region is adjacent to a section of the wall of said cavity having an area between 5% and 90% of the entire area of the wall of the cavity.

In again another embodiment said pre-selected at least one bone region is adjacent to a wall section and has the form of a shell limited by a central angle between 30° and 270°. Thus, the bone cement can be applied to a region with a dense trabecular structure by producing a new path of least resistance through selected irrigation instead of applying the bone cement to a region of the bone structure with a sparse distribution of trabeculae.

In a further embodiment said cavity extends along a longitudinal axis to a depth L wherein said selected at least one bone region is adjacent to a wall section and has the form of an annulus limited by a coaxial height I between 10% and 90% of the depth L. This has the advantage that the bone cement can be applied on the contralateral side of an obliquely fractured bone such improving the region of the bone where the thread of the bone screw engages.

In another embodiment said fluid jet lavage is applied in a pulsed manner.

In still another embodiment said fluid jet lavage is applied with a minimum frequency of 1300 pulses/min., preferably of 1400 pulses/min.

In again a further embodiment said fluid jet lavage is applied with a maximum frequency of 1700 pulses/min., preferably of 1600 pulses/min.

In another embodiment the maximum duration of one jet lavage pulse is 0.015 s, preferably 0.011 s.

In a further embodiment the minimum duration of one jet lavage pulse is 0.005 s, preferably 0.009 s.

In another embodiment the interval between two jet lavage pulses is at least 0.02 s, preferably at least 0.025 s.

In another embodiment the interval between two jet lavage pulses is at most 0.04 s, preferably at most 0.035 s.

In a further embodiment the jet lavage is performed with a maximum speed of the lavage liquid of 55 m/s, preferably of 51 m/s.

In still a further embodiment the jet lavage is performed with a minimum speed of the lavage liquid of 45 m/s, preferably of 49 m/s.

In yet another embodiment the maximum penetration depth of the jet lavage liquid is 16 mm, preferably 14 mm.

In again another embodiment the applied bone cement is a pharmaceutically loaded bone cement. Prophylactic augmentation of osteoporotic bone with pharmaceutically loaded cements allows to enhance primary mechanical properties of the bone to be treated and permits a reduction of the susceptibility to fracture. Further, during eventual resorption of the pharmaceutically loaded cement, the osteogenic drug can be released and lead to a local enhancement of the bone structure. The application of jet lavage facilitates cement distribution to the specific regions and minimizes the amount of bone cement needed for the procedure. Amounts of bioactive, pharmaceutically loaded bone cements can be reduced to a minimum in order to achieve a very local therapeutic effect, hence reducing systemic reactions to the applied drug and achieving lower adverse reactions to the setting process of cements (exothermic, acid-base reactions etc.). Further, the amount of an expensive bioactive bone cement used can be minimized.

In a further embodiment the bone cement is loaded with at least one pharmaceutical from the groups of: osteogenic drugs, osteoconductive and/or osteoinductive components, transforming growth factors (TGF-beta), osteocalcine, calcium binding proteins (GLA), bone morphogenetic protein (BMP), antimicrobial drugs or vitamins and antibiotics.

In still a further embodiment said at least one bone region is situated in a femoral head and/or a femoral neck situated essentially on one side of a plane going through the central axis of a longitudinal implant to be implanted in said bone region. This allows the advantage of applying the bone cement to a region which is situated essentially on one side of a plane going through the central axis of a longitudinal implant to be implanted in said bone region. In case of a femoral neck screw (e.g. Dynamic Hip Screw) said bone region is located at a bone portion of the femoral head, respectively of the femoral neck which is situated in a cranial direction with respect to the implant such allowing that the bone cement can be applied to that region where the thread or blades of an implanted hip or lag screw would cut into the bone structure when a load is applied from cranial e.g. due to the weight of the patient.

In yet another embodiment the fixation of a bone fixation means in said cavity is performed subsequent to said introduction of a freshly mixed bone cement, in particular for the treatment of femoral neck fractures, preferably when the cement has not yet hardened. Due to the fact that the crucial element for fracture fixation is the quality of the bone an improved anchorage of the hip screw in the femoral head can be achieved by means of an application of bone cement at selected regions.

The method according to the invention can also be used for the prophylactic augmentation of bones with severe osteoporosis. This allows the advantage that due to the prophylactic reinforcement of osteopenic or osteoporotic bone, e.g. on the contralateral side of a fractured bone, an enhancement of the bone quality (and in case that an implant is used later: an enhancement of the implant purchase in said reinforced bone) is achieved. Usually the cavity is filled with bone cement, but not necessarily, the cavity could be left as such or could be only partially filled with bone cement, e.g. at the walls.

EXAMPLE 1

(Preparation of the Bone Structure Necessary for a Treatment of Fractures at the Proximal Femur, e.g. Femoral Neck Fractures, Compression Fractures of the Proximal Tibia, Condylar Fractures of the Distal Femur or Fractures of the Distal Radius)

The method essentially comprises the steps of:

A) determining a region in the bone structure of a proximal femur where the trabecular bone structure is to be augmented. The determination of such regions is performed either selected by general anatomical considerations (where a weakened bone structure is known to occur usually) or specifically for a given patient by medical image techniques as e.g. X-ray or MRI. Here, said region in the bone structure is situated in a femoral head situated essentially on one side of a plane going through the central axis of a longitudinal implant which is to be inserted in said cavity, i.e. at the region where the vertical load exerted onto the femoral head, e.g. due to the weight of the patient transferred to the implant, e.g. the hip screw.

B) producing the cavity with a desired depth L and communicating with said bone region determined under step A, e.g. by drilling a hole in the proximal femur passing the femoral neck and partially penetrating the femoral head. The hole is drilled in such manner that it communicates with said bone structure.

Else, the cavity could be formed by indentation of a pin or k-wire or similar, where the indentation device will be removed after indentation. Also, an instrument shaped as the later implant or the implant itself could be inserted, e.g. also allowing for irrigation through its cannulation and radial perforations.

C) applying a fluid jet lavage towards said bone region determined under step A by means of a fluid jet lavage device as known in the art. A cannula (instrument) or implant for the selective irrigation of the bone structure surrounding the previously created cavity through jet lavage has at least two holes or slots, covering a radial outlet angle of less than 270°. The axial distribution of the at least two holes or slots can be both symmetrical and asymmetrical, where the length of the slots is smaller than the depth L of the created cavity. The diameter of the irrigation cannula is less than the diameter of the previously created cavity.

The fluid jet lavage is directed to the selected bone regions by means of the cannula having radial perforations only at certain locations and/or by moving the cannula axially and/or by rotating the cannula.

During irrigation the fluid jet lavage device and/or the cannula is guided manually under direct visual control and/or under image guided control. In the latter case the irrigation liquid can comprise an X-ray opaque substance. Further, the cannula can be radiopaque itself.

D) providing bone cement to said bone region, e.g. by means of a cannula and an appropriate injection means, e.g. a syringe. The bone cement is provided to said selected region either by using cannulas or implants having similar radial perforations as in case of the fluid jet lavage performed under step C or solely by virtue of the enhanced possibility of the bone cement to penetrate into the regions which are better irrigated. In the first case the bone cement is directed to the selected regions by means of a cannula having radial perforations only at certain locations and/or by moving the cannula axially and/or by rotating the cannula. During the application of the bone cement the cannula is guided manually and/or under image guided control.

E) the implant, e.g. hip screw can be inserted into said cavity as follows:
  i) after producing said cavity under step B when an implant having radial perforations as mentioned under steps C and D (allowing fluid jet lavage and application of bone cement) is used;
  ii) after irrigating the bone structure surrounding said cavity under step C when an implant having radial perforations as mentioned under step D (allowing the application of bone cement) is used; or
  iii) subsequently in the bone region having already been reinforced.

EXAMPLE 2

(Prophylactic Reinforcement of Osteopenic or Osteoporotic Bone where the Risk of e.g. a Femoral Neck or Trochanteric Fracture is High)

The method according to example 2 essentially comprises the steps of:
A) determining regions in the bone structure of a proximal femur where the trabecular structure has to be prophylactically reinforced. The determination of such regions is performed either selected by general anatomical considerations (where a weakened bone structure is known to occur usually) or specifically for a given patient by medical image techniques as e.g. X-ray or MRI. Additionally, to a bone fracture which has already occurred on one side of a patient's body a similar bone fracture on the other, healthy side can be expected due to the "fracture pattern" of the already affected side. By reason of the "fracture pattern" the healthy side can be reinforced consequently.
B) producing the cavity communicating with said bone region, e.g. drilling a hole in the proximal femur which is in communication with said bone region;
C) applying a fluid jet lavage towards said region determined under step A by means of a fluid jet lavage device as known in the art. Thereto the fluid jet lavage is directed to the selected regions by means of e.g. a cannula having radial perforations only at certain locations and/or by moving the cannula axially and/or by rotating the cannula. During irrigation the fluid jet lavage device and/or the cannula is guided manually under direct visual control and/or under image guided control. In the latter case the irrigation liquid can comprise an X-ray opaque substance and the cannula can/should also be radiopaque.
D) providing bone cement to said bone region by means of a cannula and an appropriate injection means, e.g. a syringe. The bone cement is provided to said selected region in the bone structure either by using similar cannulas as in case of the fluid jet lavage performed under step C or solely by virtue of the enhanced possibility of the bone cement to penetrate into the region which are better irrigated. In the first case the bone cement is directed to the selected regions by means of a cannula having radial perforations only at certain locations and/or by moving the cannula axially and/or by rotating the cannula. During the application of the bone cement the cannula is guided manually and/or under image guided control.

EXAMPLE 3

(Preparation of the Bone Structure Necessary for a Treatment of Fractures of the Proximal Femur)

The method according to example 3 essentially comprises the steps of:

A) determining a plurality of regions in the bone structure of a proximal femur where the trabecular bone structure is to be augmented in order to enhance purchase to the implant. The determination of such regions is performed analogously to example 1.
B) producing the cavity with a desired depth L and communicating with said bone regions determined under step A analogously to example 1.
C) applying a fluid jet lavage towards said bone regions determined under step A by means of a fluid jet lavage device as known in the art. The cannula (instrument) or implant for the selective irrigation of the bone structure used as well as its direction and the control of the fluid jet lavage is performed analogously to example 1.
D) providing bone cement to all of said bone regions e.g. by means of a cannula and an appropriate injection means, e.g. a syringe: During the filling of all prepared bone regions with bone cement pressure is applied for infiltration. Further, bone cement is applied to augment said bone regions and connect the plurality of augmented bone regions determined under step A.

A BRIEF DESCRIPTION OF THE DRAWINGS

Several embodiments of the invention will be described in the following by way of example and with reference to the accompanying drawing in which:

FIG. 2 illustrates a perspective view of a further embodiment of a cannula according to the invention;

FIG. 3 illustrates a magnified perspective view of a front portion of FIG. 1;

FIG. 4 illustrates a sectional view of a proximal femur with an injection cannula for bone cement inserted in a cavity in the bone;

Figure 1:
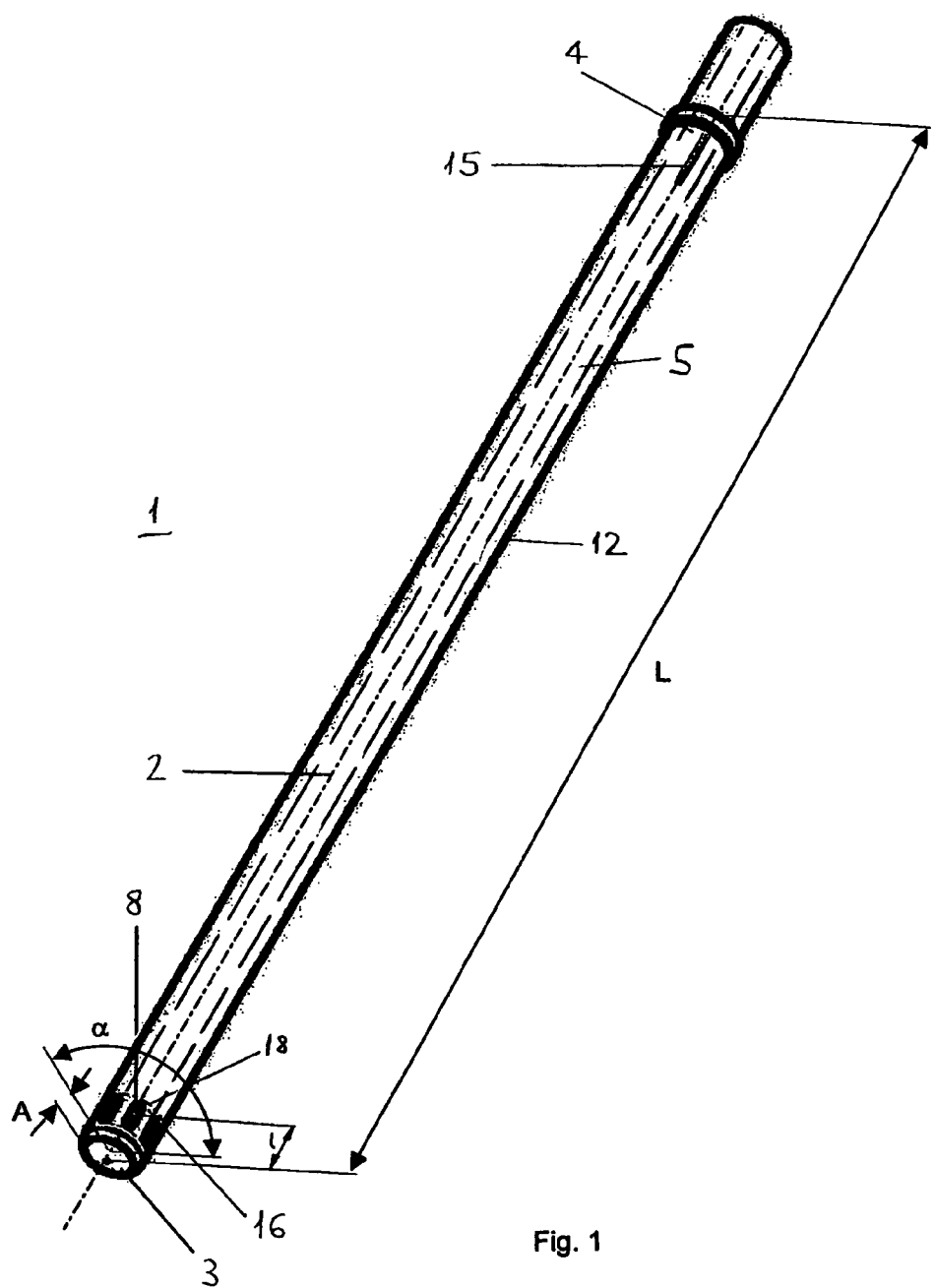
FIG. 1 illustrates a perspective view of one embodiment of a cannula according to the invention.

FIG. 1 exemplarily shows one embodiment of a cannula 1 essentially comprising a central axis 2, a front end 3, a rear end 4 and a channel 5 coaxial or parallel to said central axis 2 and defining a peripheral wall 12 of said cannula 1. Further, referencing means 15 are provided at said rear end 4, so that said cannula 1 can be brought in a desired position relative to a cavity 120 in a bone (FIG. 4). Said cannula 1 comprises three perforations 8 penetrating said peripheral wall 12 transversely to said central axis 2, wherein said three perforations 8 are arranged in a portion 16 of said peripheral wall 12 which extends over an arc orthogonal to said central axis 2 with a central angle α of about 120°. Said cannula 1 is axially closed at said front end 3.

Said cannula 1 has a length L measured parallel to said central axis 2 and said portion 16 of said peripheral wall 12 extends over a length I amounting to about 5% of said length L measured from said front end 3 of said cannula 1. Further, said perforations 8 are all located at the same distance A from said front end 3 of said cannula 1.

As shown in FIG. 3 said perforations 8 are configured as elongated holes with their long axes in the direction of said central axis 2. Said elongated holes have a length a measured parallel to said central axis 2 and a width b measured orthogonal to said central axis 2.

Said referencing means 15 comprises a marking on the peripheral surface of said cannula 1 and arranged at said rear end 4 of said cannula 1. Said marking allows to indicate the angular position of said arc 18 of said peripheral wall 12 viewed in a cross-section of said cannula 1 orthogonal to said central axis 2. Further, said referencing means 15 is located in such manner that it indicates the point of symmetry of said arc 18 of said peripheral wall 12.

FIG. 2 illustrates another embodiment of said cannula 1 which differs from the embodiment of FIG. 1 only therein that said central angle a is smaller and that said referencing means 15 is located and configured in such manner that it completely extends between the lateral limitations of said arc 18 of said peripheral wall 12.

FIG. 4 illustrates a proximal femur 100 where the trabecular bone structure is to be augmented in a direction cranial to a plane containing the axis of the implant. A cavity 120 with a depth Z in the form of a drilled hole penetrates the proximal femur 100 passing the femoral neck 102 and partially penetrating the femoral head 103.

Said cavity 120 is produced at a location such that the selected bone region is situated adjacent to the periphery of the wall of said cavity 120. The selected bone region is completely within the femoral head 103 and does not extend over the fracture site 105. Also, said bone region is directed towards the proximal end 104 of the femur, i.e. at the region where the vertical load exerted onto the femoral head 103, e.g. due to the weight of the patient is transferred to the hip screw.

Without irrigation by fluid jet lavage a bone cement subsequently injected through an injection cannula 110 as indicated by arrow A (FIG. 4) would follow a path of least resistance 114, i.e. would infiltrate into that portion of the bone structure surrounding said drilled hole which has a sparse distribution of trabeculae. Due to the large bone interstices the bone cement would be applied to a portion of the bone which would not allow a firm fixation of the hip screw. Further, the bone cement would mainly be applied in a region below said drilled hole.

Due to the directed irrigation by fluid jet lavage a removal of bone marrow and/or fat from bone interstices in the denser trabecular bone structure is achieved. Since the penetration of the bone cement depends on the extent of marrow removal from the bone interstices the now injected bone cement will follow a new, other path of least resistance 115. Hence, the bone cement will now mainly be applied in the region above said drilled hole, i.e. directed towards the cranial end of the femoral head, respectively the femoral neck such allowing to improve the anchorage of the subsequently inserted hip screw due to its anchorage in a reinforced trabecular bone structure.

Figure 5:
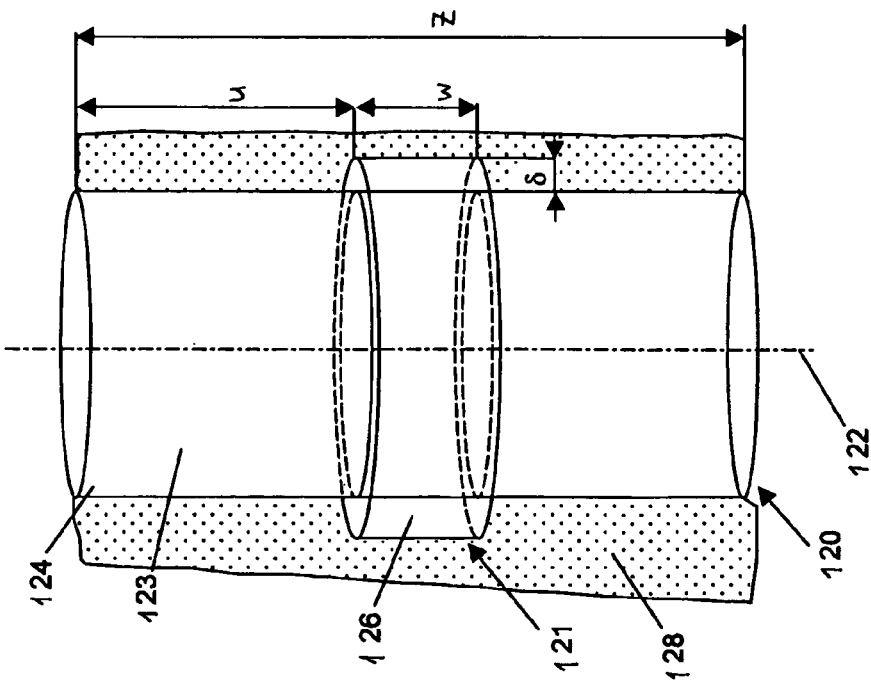
FIG. 5 illustrates a schematic representation of the irrigated wall section of the cavity according to one embodiment of the invention.

FIG. 5 illustrates an embodiment wherein the selected bone region is a wall section 121 of the bone structure 128 surrounding said cavity 120 and has the form of an annulus 126 adjoining the periphery of said cavity 120, i.e. said drilled hole 123, whereby said annulus 126 is located at a distance U from the bottom 124 of the drilled hole 123 and has a thickness δ measured perpendicularly to said longitudinal axis 122 of said drilled hole 123. Further, said annulus 126 has a length w measured parallel to the longitudinal axis 122 of said drilled hole 123 and amounting to between 10% and 90% of the depth Z of said drilled hole 23.

Figure 6:
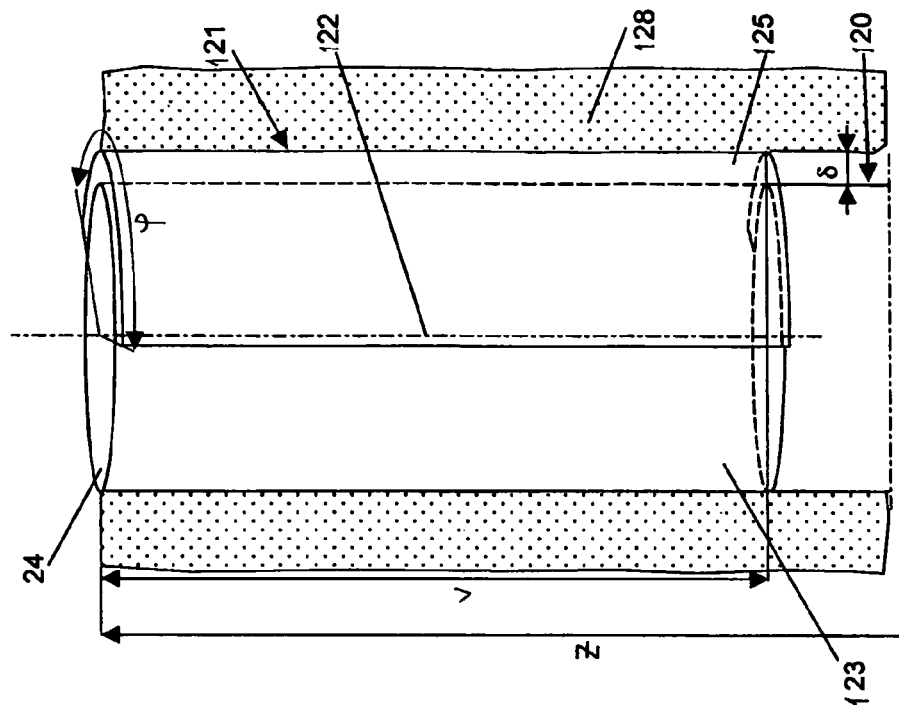
FIG. 6 illustrates a schematic representation of the irrigated wall section of the cavity according to another embodiment of the invention.

FIG. 6 illustrates an embodiment wherein the selected bone region is a wall section 121 of the bone structure 128 surrounding said cavity 120 and has the form of a shell 125 adjoining the periphery of said cavity 120, i.e. said drilled hole 123, whereby said shell 125 has a cross section perpendicular to the longitudinal axis 122 of said drilled hole 123 with the area of a sector of a circular ring having its centre on the longitudinal axis 122 and having a central angle φ of less than 270° and with a thickness δ. Further, said shell 125 has a length v measured from the bottom 124 of said drilled hole 123 and amounting to less than 90% of the depth Z of said drilled hole 123 excluding the entry part of the drilled hole into the bone and the fracture lines.

Figure 7:
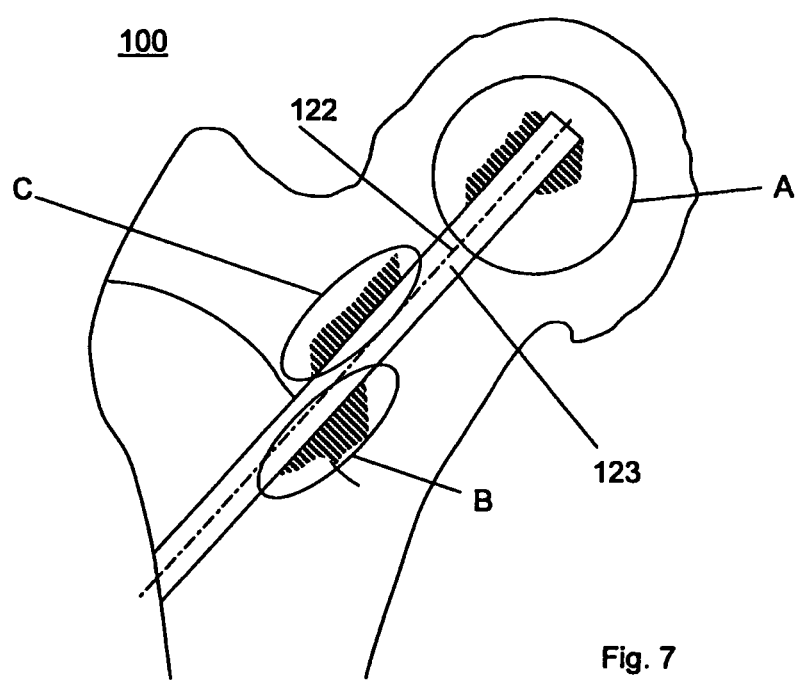
FIG. 7 illustrates a schematic view of the proximal femur in another application of the method according to the invention.

FIG. 7 exemplarily illustrates the preparation of the bone structure necessary for a prophylactic treatment of the proximal femur. In this example a plurality of bone regions which are to be provided with bone cement is selected, namely:
 a region A. In another application of the method in this region A the thread of an implant e.g. a lag screw to be implanted could also be anchored in the bone;
 a region B in the rear shaft portion of the implant. Regarded with respect to a plane in which the longitudinal axis 122 of the drilled hole 123 entirely lies in said region B is situated on this side of said plane which is directed towards the distal end of the femur; and
 a region C in an intermediate shaft portion of the implant. Regarded with respect to the plane in which the longitudinal axis 122 of the drilled hole 123 entirely lies in said region C is situated on the cranial side of said plane.

Further, the remaining sections of the wall surrounding the drilled hole 123 which connect said selected bone regions A, B and C are also provided with bone cement in order to form bridges which connect the augmented bone regions A, B and C in the lateral/medial direction. By this means the stiffness of the bone structure is improved.

What is claimed is:

1. A cannula comprising:
 a central axis, a front end, a rear end and a channel coaxial or parallel to said central axis that defines a peripheral wall of said cannula; at least two perforations penetrating said peripheral wall; and a referencing means at said rear end for bringing said at least two perforations of said cannula in a desired angular position relative to a cavity in a bone; wherein said at least two perforations are arranged within an arcuate portion of said peripheral wall that subtends a central angle α<270° having a vertex on said central axis, wherein said referencing means comprises a marking on the peripheral surface indicating the angular position of said at least two perforations, and wherein the sum of cross sectional areas of the entirety of said at least two perforations is smaller than or equal to the cross sectional area of said channel.

2. The cannula of claim 1, wherein said at least two perforations are arranged in at least two sections which are axially distanced from each other.

3. The cannula according to claim 1, wherein said at least two perforations are staggeredly arranged with respect to said central axis.

4. The cannula according to claim 1, wherein said cannula comprises between two and ten perforations arranged in said portion of said peripheral wall.

5. The cannula according to claim 1, wherein said referencing means is located in such a manner that it indicates a point of symmetry of said arcuate portion of said peripheral wall.

6. The cannula according to claim 1, wherein said referencing means is located and configured in such a manner that it completely extends between the lateral limitations of said arcuate portion of said peripheral wall.

7. The cannula according to one claim 1, wherein the sum of all cross sectional areas of said perforations is at least 0.2 mm$^2$.

8. The cannula according to claim 1, wherein the sum of all cross sectional areas of said perforations is at most 800 mm$^2$.

9. The cannula according to claim 1, wherein no perforations penetrate said peripheral wall of said cannula in a remaining part outside said portion of said peripheral wall.

10. The cannula according to claim 1, wherein said at least two perforations are arranged in a front part of said cannula.

11. The cannula according to claim 1, wherein said cannula has a length L measured parallel to said central axis and said portion of said peripheral wall extends over a length I in a range between 5% and 30% of said length L measured from said front end of said cannula.

12. The cannula according to claim 1, wherein said central angle $\alpha$ is greater than 30°.

13. The cannula according to claim 1, wherein said perforations are elongated holes with their long axes in the direction of said central axis.

14. The cannula according to claim 1, wherein said perforations are all located at the same distance A from said front end of said cannula.

15. The cannula according to claim 1, wherein said cannula is axially closed at said front end.

16. The cannula according to claim 1 additional comprising a wire and wherein
said channel is axially open at said front end; and
the cross section of said channel has a contraction with a diameter $d_i$ located between the front most of said at least two perforations and said front end which is formed as a sealing between said wire and said channel.

17. A kit for liquid jet irrigation of bone comprising a cannula according to claim 1 and a liquid jet washing apparatus including at least a pump and a control means.

18. The kit according to claim 17, wherein said liquid jet is generated in a pulsed manner.

19. The kit according to claim 17 additionally comprising at least one bone fixation implant.

20. The kit according to claim 19 additionally comprising at least one package of unmixed bone cement.

21. A kit according to claim 20 additionally comprising at least one container with washing solution.

* * * * *

UNITED STATES PATENT AND TRADEMARK OFFICE
CERTIFICATE OF CORRECTION

PATENT NO. : 8,475,464 B2
APPLICATION NO. : 12/663031
DATED : July 2, 2013
INVENTOR(S) : Gisep et al.

It is certified that error appears in the above-identified patent and that said Letters Patent is hereby corrected as shown below:

On the Title Page Item [63] should read

--[63] Related U.S. Application Data US 11/757,781, filed on June 4, 2007, now abandoned.--

Signed and Sealed this
Seventh Day of January, 2014

Margaret A. Focarino
*Commissioner for Patents of the United States Patent and Trademark Office*